US006635048B1

(12) United States Patent
Ullestad et al.

(10) Patent No.: US 6,635,048 B1
(45) Date of Patent: Oct. 21, 2003

(54) IMPLANTABLE MEDICAL PUMP WITH MULTI-LAYER BACK-UP MEMORY

(75) Inventors: David C. Ullestad, Maple Grove, MN (US); Irfan Z. Ali, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,566

(22) Filed: Apr. 28, 2000

Related U.S. Application Data

(63) Continuation-in-part of application No. 09/303,032, filed on Apr. 30, 1999, now Pat. No. 6,282,450.

(51) Int. Cl.[7] .............................................. A61N 1/08
(52) U.S. Cl. ..................................... 604/890.1; 607/59
(58) Field of Search ........................ 607/59, 60, 30–32; 604/891.1

(56) References Cited

U.S. PATENT DOCUMENTS

| | | | |
|---|---|---|---|
| 4,390,022 A | 6/1983 | Calfee et al. | |
| 4,692,147 A | 9/1987 | Duggan | ........................ 604/93 |
| 5,318,593 A | 6/1994 | Duggan | |
| 5,360,437 A | 11/1994 | Thompson | ................... 607/30 |
| 5,456,691 A | 10/1995 | Snell | ........................... 607/30 |
| 5,456,692 A | 10/1995 | Smith, Jr. et al. | ............. 607/31 |
| 5,653,735 A | 8/1997 | Chen et al. | |
| 5,713,922 A | 2/1998 | King | .............................. 607/2 |
| 5,735,882 A | 4/1998 | Rottenberg et al. | |
| 5,782,798 A | 7/1998 | Rise | ............................. 604/49 |
| 5,814,014 A | 9/1998 | Elsberry et al. | ............... 604/43 |
| 5,840,069 A | 11/1998 | Robinson | ..................... 604/131 |
| 6,036,459 A | 3/2000 | Robinson | ................. 417/477.7 |
| 6,282,450 B1 | 8/2001 | Hartlaub et al. | |

FOREIGN PATENT DOCUMENTS

| | | |
|---|---|---|
| EP | 0 750 921 | 1/1997 |
| EP | 1 048 323 | 11/2000 |
| WO | WO 95/13112 | 5/1995 |
| WO | WO 99/10043 | 3/1999 |

OTHER PUBLICATIONS

European Search Report (3 pages).

*Primary Examiner*—Jeffrey R. Jastrzab
(74) *Attorney, Agent, or Firm*—Banner & Witcoff, Ltd.

(57) ABSTRACT

In a medical treatment device implanted within the body of a patient, a system and method using volatile and non-volatile memory devices within an implanted drug infusion pump to provide a safe and robust programmable system, able to back-up and restore the device's hardware and software operating parameters in the event of RAM corruption and as an alternative to hardware trim techniques. The pump includes a processor, a ROM, a RAM, and an EEPROM. The RAM serves as a main memory and the EEPROM serves a back-up memory in the event of RAM corruption. The ROM serves as an additional layer of back-up memory in the event of RAM and EEPROM corruption.

49 Claims, 5 Drawing Sheets

IMPLANTABLE MEDICAL PUMP WITH MULTI-LAYER BACK-UP MEMORY

BACKGROUND OF THE INVENTION

This is a continuation-in-part of the earlier filed patent application Ser. No. 09/303,032, filed on Apr. 30, 1999 now U.S. Pat. No. 6,282,450, entitled "System and Method for Storing Firmware in a Human-Implantable Medical Treatment Device," and invented by Jerome Hartlaub and David Ullestad for which priority is claimed. This patent application is incorporated herewith by reference in its entirety.

In addition, this patent application is related to the following patent applications filed herewith:

(1) U.S. patent application Ser. No. 09/562,221 entitled "Battery Recharge Management for an Implantable Medical Device," filed on Apr. 28, 2000, and having named inventors Nathan A. Torgerson and James E. Riekels; and (2) U.S. patent application Ser. No. 09/560,775 entitled "Power Management for an Implantable Medical Device," filed on Apr. 28, 2000, and having named inventors Nathan A. Torgerson and James Riekels.

FIELD OF INVENTION

This invention relates generally to implantable medical pumps, and more particularly to an implantable medical pump having a non-volatile programmable memory for restoring the device's hardware and software operating parameters.

DESCRIPTION OF THE RELATED ART

Implantable medical pumps can be used to treat any number of physiological, psychological, and emotional conditions. For some medical conditions, implantable medical pumps provide the best, and at times the only, therapy to restore an individual to a more healthful condition and a fuller life.

The medical pump provides the patient with a programmable level of dosage or infusion of a drug or other therapeutic agent. The pump typically includes a drug reservoir, a fill port, a peristaltic pump having a motor and a pumphead to pump out the drug from the reservoir, a catheter port to transport the drug from the reservoir via the pump to a patient's anatomy, and the electronics to control the motor. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing. The peristaltic pumps use rollers which move along a pump tube, thereby moving liquid through the tube. Some form of fluid flow control is also provided to control or regulate the flow of fluid medication from the reservoir to the outlet of the device for delivery of the medication to the desired location in a body, usually through a catheter.

Examples of drug infusion pumps currently available are the SynchroMed® programmable pump sold by Medtronic, Inc. of Minneapolis, Minn., and those disclosed in U.S. Pat. No. 4,692,147 (Duggan), U.S. Pat. No. 5,840,069 (Robinson), and U.S. Pat. No. 6,036,459 (Robinson).

The drug delivery pump also includes electronics (typically a processor and associated other hardware) to provide a prescribed dosage of drug under a set time schedule. Various treatment parameters such as the dosage, the rate and timing prescribed by the clinician are entered into the pump using an external computer-like device called a physician programmer and stored in a Random Access Memory (RAM). The programmer communicates with the pump by telemetry. This also allows the clinician to determine how the pump is operating at any given time. The clinician can also can use the programmer to change the treatment parameters such as the medication dosage. The various electrical components of the pump such as the processor and the memory devices, except the power source, can be designed using on one or more Application Specific Integrated Circuits (ASICs).

Once the pump is implanted, however, any number of complications may occur. For example, the RAM, which stores the treatment parameters for the drug therapy, may become corrupted. Corruption of the RAM may occur for any number of reasons including for example: (1) a temporary drop in the device's battery voltage (due to Electro-Magnetic Interference (EMI) or an internal power surge); (2) software execution malfunctions (such a bug or a temporary bit flip within the processor which causes erroneous program execution); or (3) latent RAM cell failures where the RAM cell loses its ability to hold programmed values over time. If the RAM is corrupted, the pump must be reprogrammed. However, until the pump is reprogrammed, the pump cannot operate. This is undesirable since the patient loses the drug treatment therapy during this time and may even go into withdrawal.

Another example of a complication is that it may become necessary to adjust trim parameters stored within the ASIC. Trim parameters are default settings such as voltage references and bias currents stored in the ASIC. Each ASIC will have a unique set of trim parameter values that are calculated by electrically testing the chip and measuring the trim parameter values. Using a laser trimming process, the trim parameter values are permanently stored on the chip. This laser process trims away chip material to change characteristics of the chip including, for example, the resistance value. Again, the trim parameters values in the ASIC are permanently stored values and cannot be adjusted after manufacture. This is problematic since the trim parameters values may need to be subsequently adjusted due to a number of reasons including for example: (1) trim parameters shifting due to age; (2) a dependence to other pump components; (3) additional performance data that is subsequently gathered; or (4) simply due to manufacturing trim errors. Laser trimming is also a time consuming process.

Accordingly, it is desireable for the implantable drug pump to continue providing treatment therapy based on default settings even after detecting corruption of therapy data in memory. It is also desireable to provide an implantable drug pump with programmable trim parameters that may be adjusted after manufacture or after implant.

SUMMARY OF THE INVENTION

The present invention uses various types of volatile and non-volatile memory devices within an implanted drug infusion pump to provide a safe and robust programmable system, able to back-up and restore the device's hardware and software operating parameter values in the event of memory corruption and as an alternative to hardware trim techniques.

In a preferred embodiment, the present invention includes a processor, a Read Only Memory (ROM), a Random Access Memory (RAM), and an electrically erasable programmable read-only memory (EEPROM). The EEPROM provides a programmable non-volatile memory wherein customized operating parameter values of the pump and the trim parameter values of the integrated chip(s) may be stored. The values stored in the EEPROM may then be relied upon during times when the other memory devices become corrupted. These values may also be adjusted to account for changing conditions of the pump and the treatment therapy. Further, the ROM provides a form of non-programmable, non-volatile memory wherein a safe-mode set of parameter values may be stored. In the event that both the RAM and the EEPROM have become partially or fully corrupted, the pump may at least operate in a safe-mode. Advantageously, the present invention provides a multi-layer backup mechanism to ensure continued operation of the implantable drug pump during corruption of the memory. Further, the trim parameter values may be subsequently adjusted without having to explant the pump and replace the integrated chip(s).

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

This present invention uses various types of volatile and non-volatile memory devices within an implanted drug infusion pump to provide a safe and robust programmable system, able to back-up and restore the device's hardware and software operating parameters in the event of memory corruption and as an alternative to hardware trim techniques. In this regard, the implantable pump of the present invention utilizes a non-volatile programmable memory having stored therein "safe-mode" and customized parameter values, a non-volatile, non-programmable memory having stored therein a "safe-mode" set of parameter values, and a volatile programmable memory storing either the customized or the safe-mode parameter values. As used herein, the parameter values include parameter values for the delivery of drug from the pump to the patient and trim parameter values.

Figure 1:
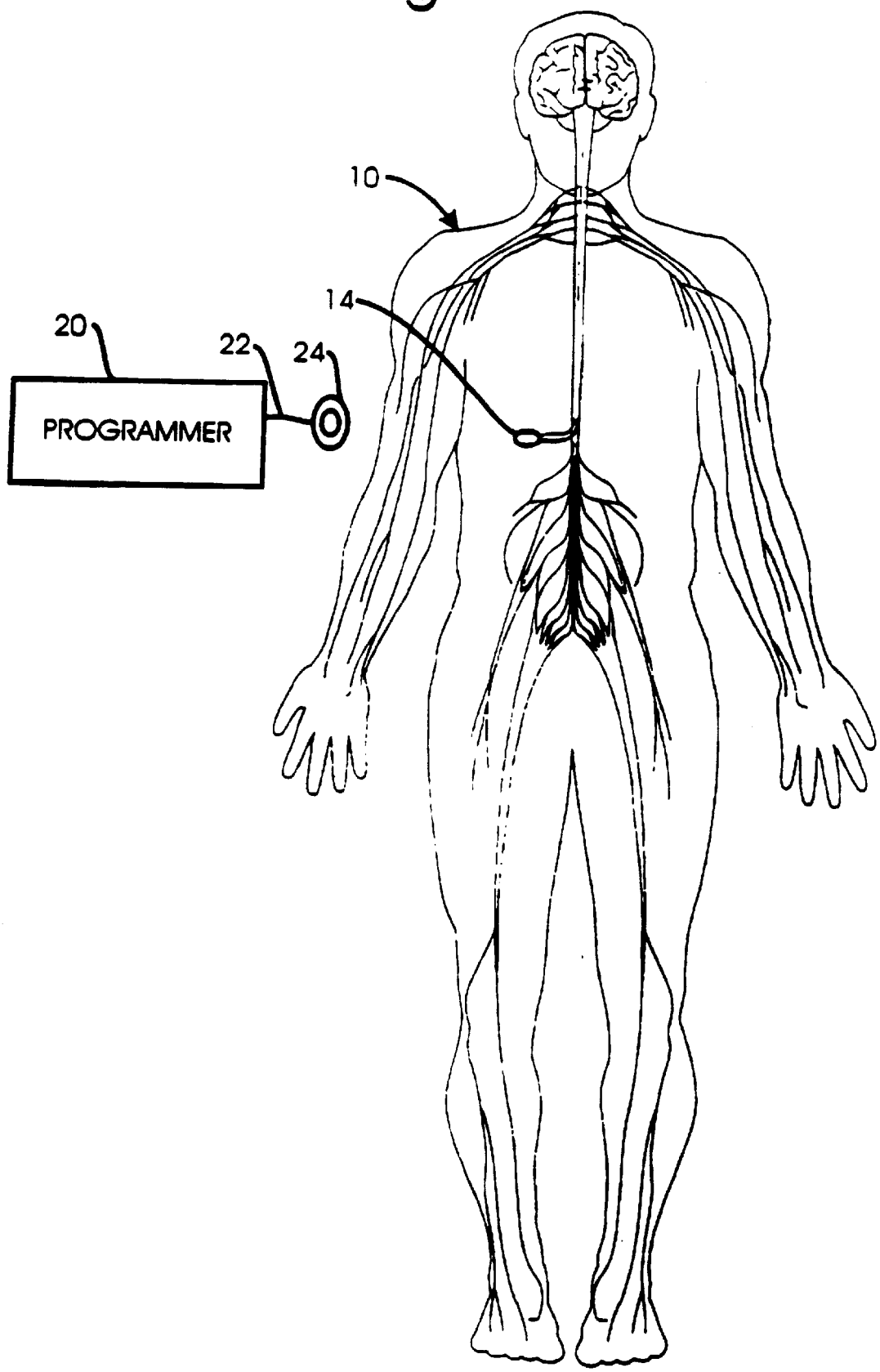
FIG. 1 is a schematic block diagram of an implantable medical pump in accordance with the present invention.

FIG. 1 is a schematic view of a patient 10 having an implantable pump 14 implanted within the patient's body. The implantable pump 14 is programmable through a telemetry link from programmer 20, which is coupled via a conductor 22 to a radio frequency antenna 24. The external programmer 20 may be a patient programmer, a physician programmer, or a manufacturing programmer (for adjusting trim parameter values). The pump 14 includes one or more drugs that are delivered to a predetermined portion of the patient's body via one or more catheters.

Figure 2:
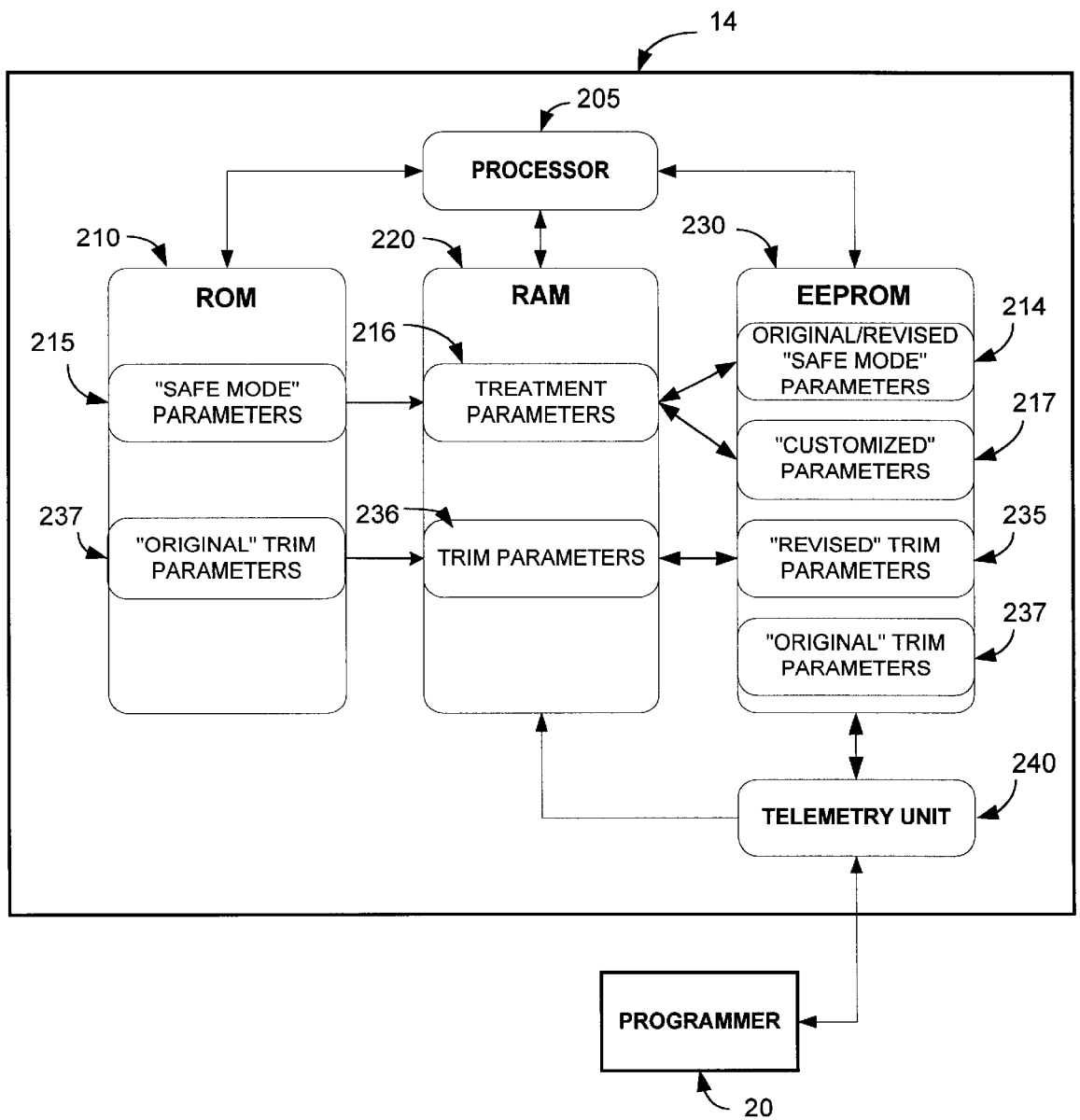
FIG. 2 is a schematic block diagram showing the relevant componentry of an implantable medical pump in accordance with the present invention.

FIG. 2 is a schematic block diagram of the relevant componentry within the implantable pump 14 in accordance with a preferred embodiment of the present invention. In a preferred embodiment, the implantable pump 14 includes a processor 205, a Read Only Memory (ROM) 210, a Random Access Memory (RAM) 220, and an electrically erasable programmable read-only memory (EEPROM) 230. The processor 205 controls the drug delivery to the patient in accordance with the drug delivery parameter values stored in memory. The ROM 210 is a non-volatile, non-programmable memory commonly used for default values, constants, and executable program instructions. As used herein, the ROM 210 includes any such non-volatile, non-programmable memories. The RAM 220 is a volatile, programmable memory commonly used for dynamic or programmable values. The RAM 220 is also used for executable program instructions where a ROM-based "boot loader" supports the loading of program instructions during normal operation. As used herein, the RAM 220 includes any such volatile, programmable memories including but not limited to a Ferroelectric Random Access Memory (FRAM), a Dynamic Random Access Memory (DRAM), or a Static Random Access Memory (SRAM). The EEPROM 230 is a form of a nonvolatile, programmable memory. As used herein, the EEPROM 230 includes any such non-volatile, programmable memories including, but not limited to, a flash EEPROM 230, a non-volatile RAM (NVRAM), or a digital logic circuit. Each of these components may be configured on one or more Application Specific Integrated Circuits (ASICs). Trim parameter values for the ASIC may be stored in programmable hardware registers. The processor 205 is coupled to the memory devices via a bidirectional data bus.

In accordance with the present invention, the ROM 210 has stored therein a "safe-mode" set of parameter values 215 and 237. These parameter values 215 and 237 provide a last-resort drug treatment schedule in the event that the other memory devices 220 and 230 have been corrupted and allows continued operation of the drug pump 14 in these circumstances. The "safe-mode" parameter values 215 and 237 may be stored in the ROM 210 at fabrication and may vary depending upon the ailment being treated and/or the particular needs of the patient 10. The "safe-mode" parameters 215 and 237 are determined based on the drug, the concentration of the drug, and the therapy to be provided. The safe-mode parameters 215 and 237 are designed to remain unchanged throughout the treatment program.

The EEPROM 230 has stored therein a "customized" set of parameter values 217 and 235. These parameter values 217 and 235 provide treatment therapy that best suits the particular need of the patient 10. These parameter values 217 and 235 are designed to be changing to accommodate the changing needs of the patient 10 and to provide a mechanism to fine-tune the treatment therapy. The customized parameter values 217 and 235 may be revised via telemetry unit 240 using the external programmer 20. The EEPROM 230 also has stored therein a revised/original "safe-mode" set of parameter values 214. The original "safe-mode" parameter values 214 may be adjusted by the external programmer 20 to form a revised set of "safe mode" parameter values 214. In this regard, the EEPROM 230 serves to provide another location for the RAM 220 to look to for safe mode parameter values in the event of memory corruption. For example, if the RAM 220 is fully corrupted and the EEPROM 230 is only partially corrupted with the corruption being in the customized set of parameter values 217, the safe-mode parameter values 214 in the EEPROM 230 may be retrieved.

The original safe-mode parameter values 215 stored in the ROM 210 may be retrieved as a last resort in the event that both the RAM 220 and the EEPROM 230 are fully corrupted. The EEPROM 230 may also store therein a set of original trim parameters 237.

During initialization of the implantable pump 14, parameters values 217 and 235 are copied from the EEPROM 230 into RAM 220. When it becomes desirable to subsequently modify, add, or delete one or more parameter values, the revised parameter values may be downlinked via telemetry unit 240 from the programmer 20 and stored in RAM 220. These values are then subsequently copies on to the EEPROM 230. Alternatively, the values may be stored first to the EEPROM 230 and then to the RAM 220.

RAM 220 is the primary memory for storage of the parameter values 216 and 236. EEPROM 230 and ROM 210 serve as a multi-layer back-up system to ensure against corruption. In the event of RAM corruption, RAM 220 may look first to EEPROM 230 and then to ROM 210 for parameter values. The parameter values from the EEPROM 230 or the ROM 210 may then be copied on to the RAM 220. As a result, the need to explant the implanted drug pump 14 as a result of certain latent memory failures can be avoided. At any time, the RAM 220 has stored therein either the customized parameter values 217 and 235 of EEPROM 230, the revised safe mode parameters 214 of the EEPROM 230, or the original safe-mode parameter values 215 and 237 of ROM 210. Details of a tiered fault recovery strategy for recovering from a RAM fault are set forth below.

As used herein, the above parameter values include parameter values 215 and 217 for the delivery of drug from the pump 14 to the patient (software values) as well as trim parameter values 235 and 237 (hardware values). Parameters for the delivery of drug include, for example, values for drug dosage amount, drug dosage rate, drug dosage timing, drug dosage frequency. Parameter values may be provided for each type of drug being provided by the pump 14. The trim parameter values 235 and 237 may also be adjusted over time to fine-tune or to accommodate changed circumstances. Trim parameters include, for example, values for bias current, reference voltage, and resistance values.

Figure 3:
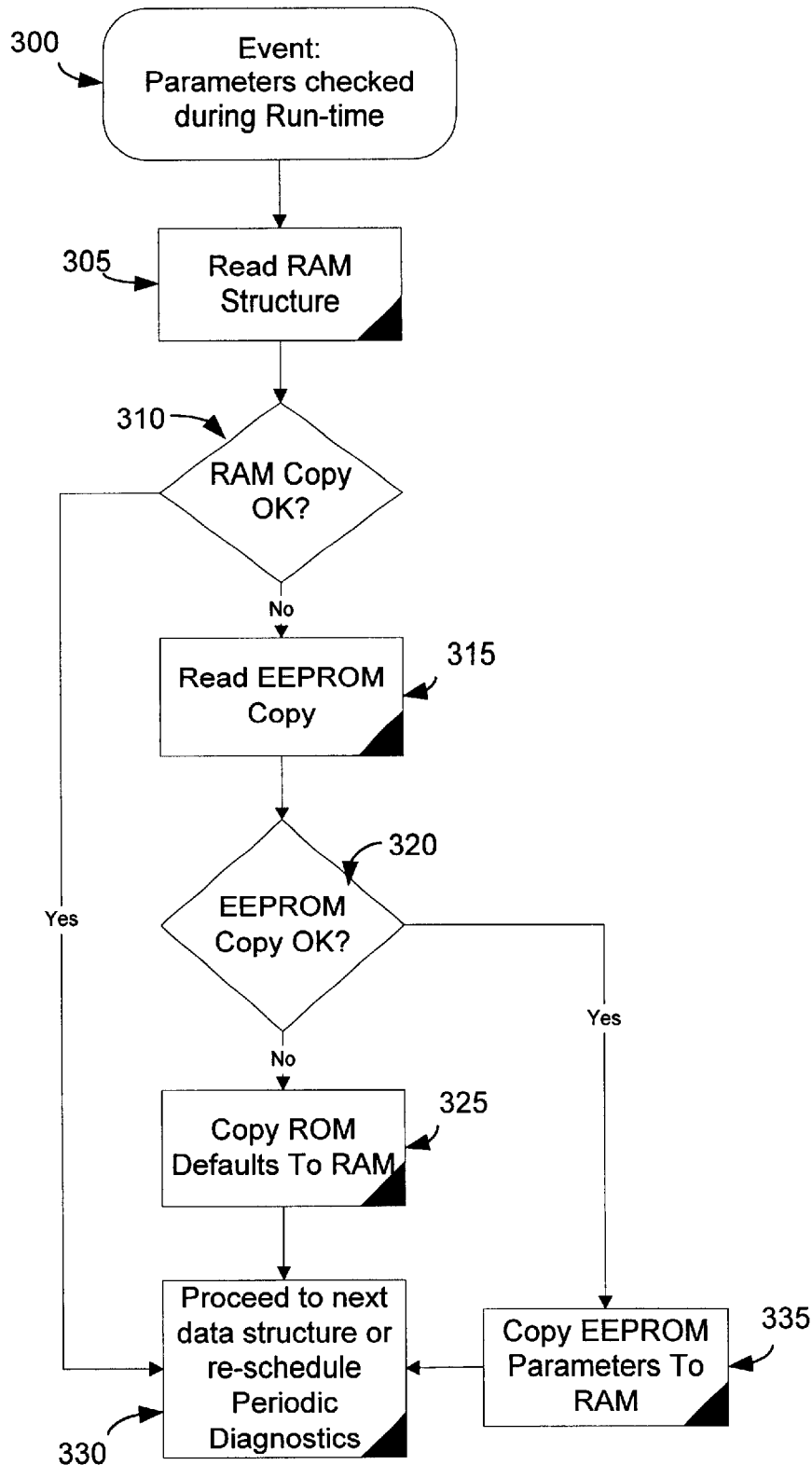
FIG. 3 is a simplified flow chart depicting steps for implementing a tiered fault recovery strategy.

FIG. 3 is a simplified flow chart illustrating the procedure for recovering data from a non-volatile memory source. During normal operation of the pump 14, the processor 205 will periodically check the parameter values 216 and 236 stored within the RAM 220 to ensure that the treatment therapy being delivered is in accordance with the parameter values 216 and 236. At step 305, the processor 205 first looks to the RAM 220 for the parameter values 216 and 236. At step 310, if the RAM copy is OK, then at step 330, the processor 205 either checks the next data structure or continues operation of the pump 14 in accordance with the parameter values 216 and 236 stored within the RAM 220. However, at step 315, if the RAM copy is somehow corrupted, the processor 205 then looks to the EEPROM 230 for the customized parameter values 217 and 235 stored therein. At step 320, if the EEPROM 230 is OK, then at step 335, the customized parameters 217 and 235 stored in the EEPROM 230 are copied on to the RAM 220, thereby replacing parameters 216 and 236. The processor 205 reads these values and continues on to step 330. However, at step 320, if the EEPROM copy is also somehow corrupted, the processor 205 then looks to the safe mode parameter values 215 and 237 stored in a non-corrupted part of the EEPROM 230 or ROM 210. At step 325, the safe mode parameter values 215 and 237 stored in the ROM 210 are copied on to the RAM 220, thereby replacing parameters 216 and 236.

Accordingly, as illustrated in the flow chart of FIG. 3, the EEPROM 230 and ROM 210 provide a multi-layered fault-recovery system of the hardware and software operating parameters.

Figure 4:
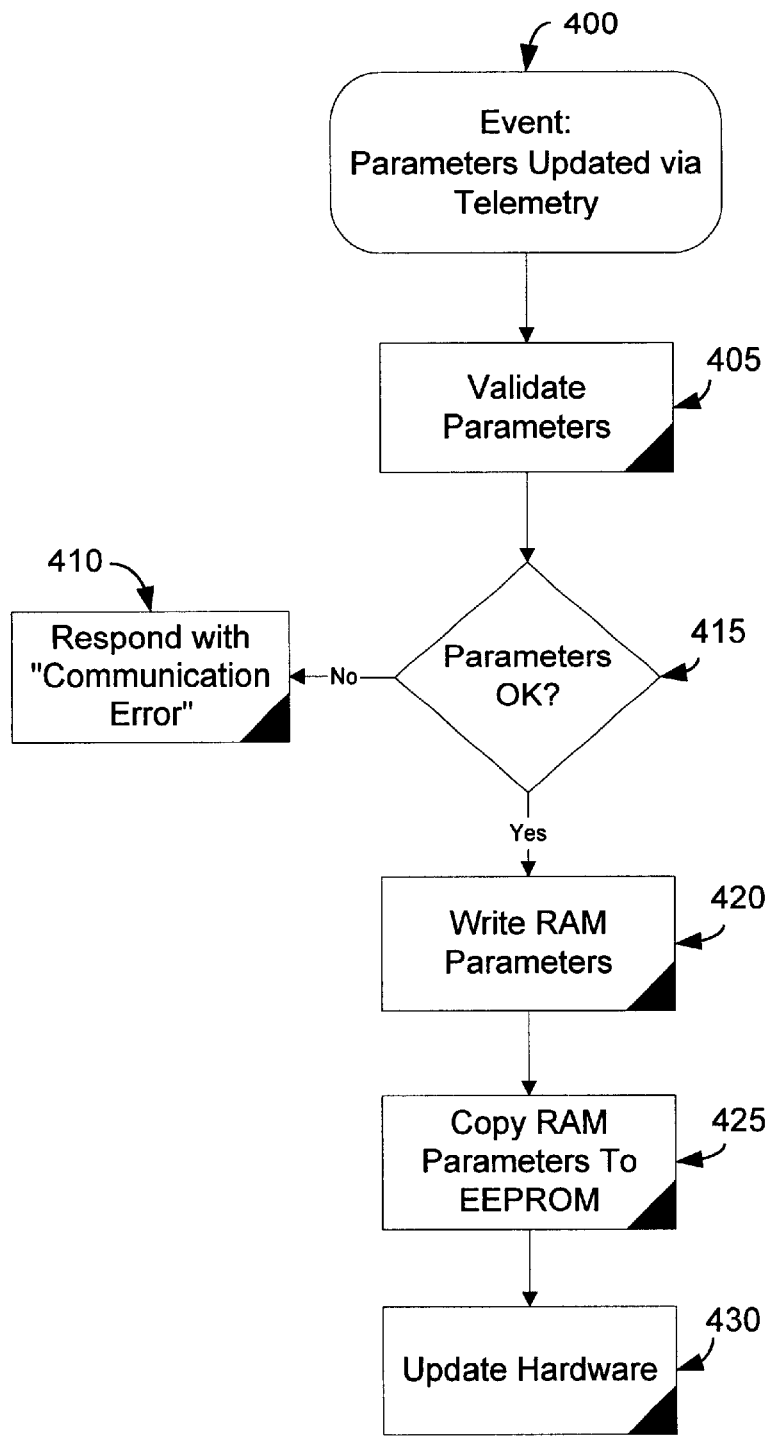
FIG. 4 is a simplified flow chart depicting steps for updating parameter values in accordance with the present invention.

As stated previously, the parameter values 216 and 236 stored in the RAM 210, and the values 217 and 235 stored in the EEPROM 230 may be revised via telemetry using the external programmer 20 to allow continued customization and fine-tuning of the pump 14. In this regard, FIG. 4 is a simplified flow chart depicting the procedure for changing parameter values 216 and 236 in the RAM 210 and values 217 and 235 in the EEPROM 230. At step 400, parameter values are downlinked via telemetry unit 240 from the external programmer 20 and stored in a temporary memory such as a cache (not shown). At step 405, the processor 205 validates the parameter values. In particular, the downlinked parameter values will be checked for data integrity. Any number of known techniques may be implemented including, for example, 2-byte CRC-16, date/size check, and/or data value boundary check. At step 415, the processor 205 determines whether the parameter values are OK. If the parameter values are not OK, at step 410, no parameter values will be updated and a communication error message is sent back to the external programmer 20. If the parameter values are OK, at step 420, the parameter values are first copied to the RAM 220. At step 425, the parameter values from the RAM 220 are copied on the EEPROM 230. In the event that the parameter values are trim parameters, then at step 430, the corresponding hardware, such as programmable hardware registers for the corresponding integrated circuit, is updated in accordance with the revised trim parameter values. Those skilled in the art will appreciate that any number of alternative procedures may be used to update the parameter values. For example, the parameter values may be first stored in the EEPROM 230 before it is stored in the RAM 220.

Figure 5:
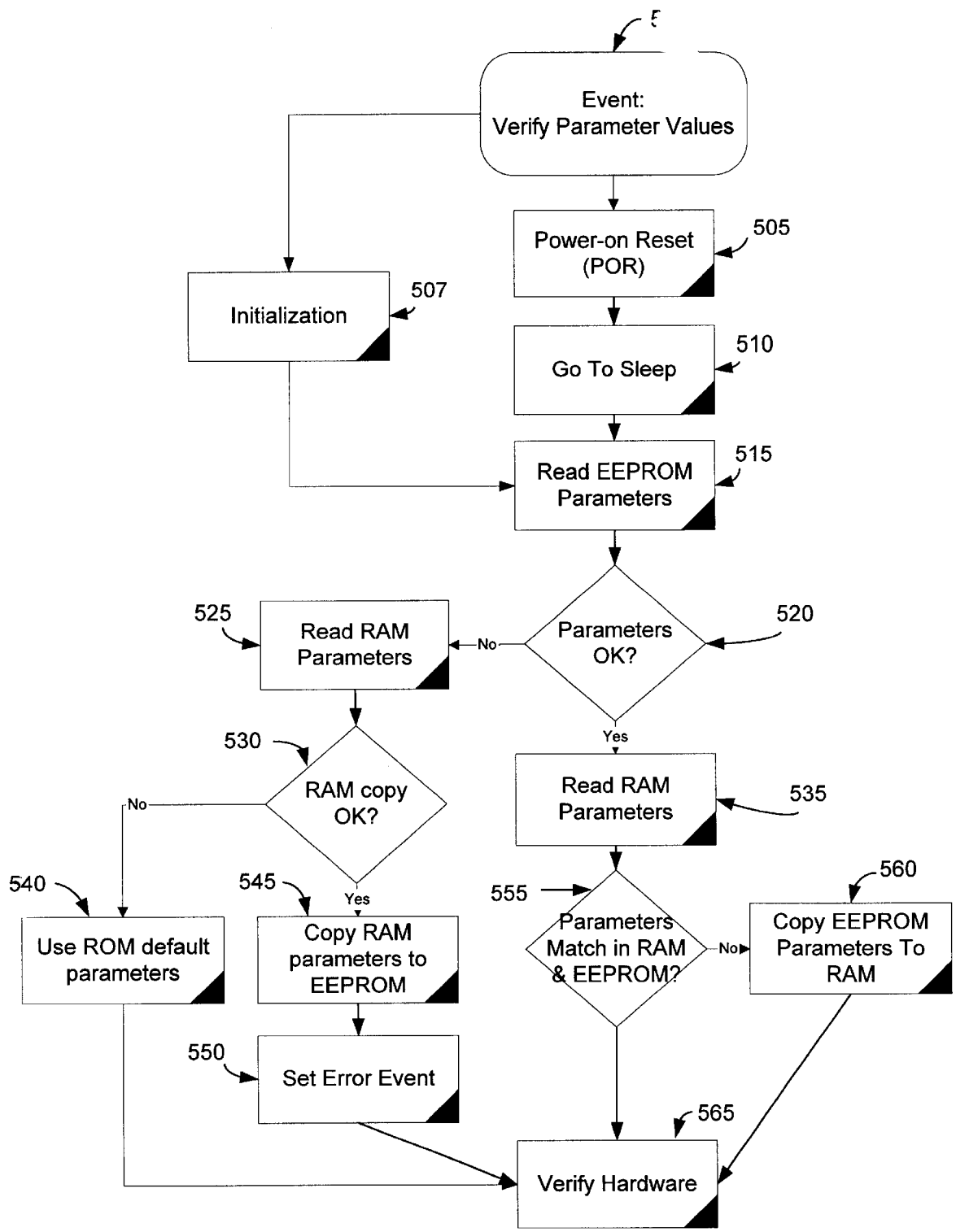
FIG. 5 is a simplified flow chart depicting steps for verifying parameter values during pump initialization or after a Power-On-Reset (POR).

During initialization, which may be necessary for a number of reasons, or after a "power-on" reset (POR), the implantable drug pump 14 typically will perform a check for valid parameter values. In this regard, FIG. 5 is a simplified flow chart depicting the procedure for setting the parameter values during a POR or pump initialization. At step 505, the POR procedure is initiated. At step 510, the pump 14 may be set to go into a sleep mode. This allows the trim parameter values to be written to the EEPROM 230 during manufacturing without telemetry. Alternatively, at step 507, the system is being initialized. In either event, at step 515, the processor 205 reads the parameter values 217 and 235 stored in the EEPROM 230 and, at step 520, validates the parameter values.

If the EEPROM parameter values 217 and 235 are not OK, at step 525, the processor 205 reads the parameter values 216 and 236 in the RAM 220 and, at step 530, checks whether they are OK. If they are not OK, then at step 540 the processor 205 resorts to the "safe mode" parameter values 215 and 237 stored in the ROM 210. The ROM parameter values 215 and 237 are then copied on the RAM 220. If they are OK, then at step 545 the processor 205 copies the RAM parameter values 216 and 236 to the EEPROM 230 and at step 550 sets an error event for uplink to the external programmer 20. In the event that the parameter values are trim parameters, then at step 565, the corresponding hardware is updated in accordance with the trim parameter values.

In an alternative embodiment, the RAM 220 may be checked before the EEPROM 230 is checked. The two sets of values may then be checked with each other to ensure data integrity.

Referring back to step 520, if the EEPROM parameter values 217 and 235 are OK, then at step 535, the processor 205 reads the parameter values 216 and 236 in the RAM 220 and, at step 555, checks whether the parameter values in the RAM 220 and EEPROM 230 match. If they do not match, the EEPROM parameter values 217 and 235 are presumed to be more reliable or more current. Accordingly, at step 560, the processor 205 copies the EEPROM parameters values 217 and 237 on the RAM 220. If they do match, then no further processing is necessary. Again, in the event that the parameter values are trim parameters, then at step 565, the corresponding hardware is updated in accordance with the trim parameter values. Those skilled in the art will appreciate that any number of alternative procedures may be used to verify the parameter values during initialization or a POR.

Although not required, the fault-recovery procedure described above is in the form of computer-executable instructions, such as program modules, stored in computer-readable medium, namely the ROM 210. Generally, program modules include routines, programs, objects, scripts, components, data structures, etc. that perform particular tasks or implement particular abstract data types.

This invention has been described with reference to certain preferred embodiments. Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

We claim:

1. A system for storing treatment parameter values in an implantable drug pump, the system comprising:
   (a) a read only memory ("ROM") having stored therein at least one safe mode parameter value;
   (b) a non-volatile, programmable memory having stored therein at least one customized parameter value; and
   (c) a random access memory ("RAM") having stored therein either the safe mode parameter value or the customized parameter value.

2. The system for storing treatment parameter values of claim 1, further comprising:
   (d) a processor providing treatment therapy to a patient in accordance with one of the parameter values.

3. The system for storing treatment parameter values of claim 1, further comprising:
   (d) a telemetry unit for updating the customized parameter value.

4. The system for storing treatment parameter values of claim 3, further comprising:
   (e) an external programmer for updating the customized parameter value via the telemetry unit.

5. The system for storing treatment parameter values of claim 1, wherein the safe mode parameter value is for operating the pump and the safe mode parameter value corresponds to a parameter selected from the group consisting of drug dosage amount, drug dosage rate, drug dosage timing, and drug dosage frequency.

6. The system for storing treatment parameter values of claim 1, wherein the customized parameter value is for operating the pump and the customized parameter value corresponds to a parameter selected from the group consisting of drug dosage amount, drug dosage rate, drug dosage timing, and drug dosage frequency.

7. A system for storing treatment parameter values in an implantable medical device, the system comprising:
   (a) a read only memory ("ROM") having stored therein at least one safe mode parameter value;
   (b) a non-volatile, programmable memory having stored therein at least one customized parameter value, wherein the customized parameter values corresponds to a trim parameter selected from the group consisting of bias current, reference voltage, and resistance; and
   (c) a random access memory ("RAM") having stored therein either the safe mode parameter value or the customized parameter value.

8. The system for storing treatment parameter values of claim 1, wherein the non-volatile, programmable memory is selected from the group consisting of an EEPROM, a flash EEPROM, and a logic circuit.

9. The system for storing treatment parameter values of claim 1, further comprising:
   (d) means for restoring the RAM, upon a RAM failure, by copying the customized parameter value from the non-volatile, programmable memory.

10. The system for storing treatment parameter values of claim 1, further comprising:
    (d) means for restoring the RAM, upon a RAM failure, by copying the safe-mode parameter value from the ROM.

11. A system for storing treatment parameter values in an implantable medical device, the system comprising:
    (a) a read only memory ("ROM") having stored therein at least one safe mode parameter value;
    (b) a non-volatile, programmable memory having stored therein at least one customized parameter value;
    (c) a random access memory ("RAM") having stored therein either the safe mode parameter value or the customized parameter value; and
    (d) means for restoring the EEPROM, upon a EEPROM failure, by copying the safe-mode parameter value from the ROM.

12. An implantable pump comprising in combination:
    (a) a processor providing controlled delivery of drug from a drug reservoir;
    (b) a first back-up memory having stored therein at least one customized parameter value;
    (c) a second back-up memory having stored therein at least one safe-mode parameter value; and
    (d) a main memory coupled to the processor having stored therein the customized parameter or the safe-mode parameter.

13. The implantable pump of claim 12, wherein the main memory is a RAM.

14. The implantable pump of claim 12, wherein the first back-up memory is a non-volatile, programmable memory.

15. The implantable pump of claim 14, wherein the non-volatile, programmable memory is selected from the group consisting of an EEPROM, a flash memory, and a logic circuit.

16. The implantable pump of claim 12, wherein the first back-up memory also has stored therein at least one safe-mode parameter value.

17. The implantable pump of claim 12, wherein the second back-up memory is a non-volatile, non-programmable memory.

18. The implantable pump of claim 12, further comprising
    (e) a telemetry unit providing communication between the pump and an external programmer.

19. The implantable pump of claim 12, further comprising:
    (d) means for restoring the main memory, upon a main memory failure, by copying the customized parameter value from the first back-up memory.

20. The implantable pump of claim 12, further comprising:
    (d) means for restoring the main memory, upon a main memory failure, by copying the safe-mode parameter value from the second back-up memory.

21. A method of restoring treatment therapy from within an implantable pump, comprising the steps of:
   (a) looking to a main memory for at least one parameter value;
   (b) if the main memory is corrupted, looking to a first back-up memory for a customized parameter value;
   (c) if the first back-up memory is not corrupted, reading the customized parameter value; and
   (d) if the first back-up memory is corrupted, reading a safe-mode parameter value from a second back-up memory.

22. The method of restoring treatment therapy of claim 21, further comprising the step of:
   (e) if the first back-up memory is not corrupted, copying the customized parameter value to the RAM.

23. The method of restoring treatment therapy of claim 21, further comprising the step of:
   (e) if the first back-up memory is corrupted, copying the safe-mode parameter value from the second back-up memory to the main memory.

24. The method of restoring treatment therapy of claim 21, further comprising the step of:
   (e) using an external programmer to update the customized parameter value via telemetry.

25. The method of restoring treatment therapy of claim 21, wherein the parameter value corresponds to a therapy parameter.

26. The method of restoring treatment therapy of claim 25, wherein the therapy parameter is selected from the group consisting of drug dosage amount, drug dosage rate, drug dosage timing, and drug dosage frequency.

27. A method of restoring treatment therapy from within an implantable medical device, comprising the steps of:
   (a) looking to a main memory for at least one parameter value wherein the parameter value corresponds to a trim parameter selected from the group consisting of bias current, reference voltage, and resistance;
   (b) if the main memory is corrupted, looking to a first back-up memory for a customized parameter value;
   (c) if the first back-up memory is not corrupted, reading the customized parameter value; and
   (d) if the first back-up memory is corrupted, reading a safe-mode parameter value from a second back-up memory.

28. A computer-readable medium having computer-executable instructions for performing the steps recited in claim 21.

29. A method of providing a multi-layer back-up memory for an implantable medical device comprising the steps of:
   (a) storing at least one customized parameter value in a first back-up memory;
   (b) storing at least one safe-mode parameter value in a second back-up memory; and
   (c) storing the customized parameter value in a main memory.

30. The method as in claim 29, further comprising the step of:
   (d) restoring the customized parameter value in the main memory from the first backup memory if a first fault in the main memory is detected and if the customize parameter value in the first back-up memory is valid.

31. A method of providing a multi-layer back-up memory for an implantable medical device comprising the steps of:
   (a) storing at least one customized parameter value in a first back-up memory;
   (b) storing at least one safe-mode parameter value in a second back-up memory;
   (c) storing the customized parameter value in a main memory; and
   (d) storing the safe-mode parameter value in the main memory from the second backup memory if a first fault in the main memory is detected and a second fault is detected in the second back-up memory.

32. A computer-readable medium having computer-executable instructions for performing the steps recited in claim 29.

33. An implantable medical device comprising in combination:
   (a) a first back-up memory having stored therein at least one customized parameter value;
   (b) a second back-up memory having stored therein at least one safe-mode parameter value; and
   (c) a main memory coupled to the processor having stored therein the customized parameter value or the safe-mode parameter value.

34. The implantable medical device of claim 33, wherein the main memory is a RAM.

35. The implantable medical device of claim 33, wherein the first back-up memory is a non-volatile, programmable memory.

36. The implantable medical device of claim 35, wherein the non-volatile, programmable memory is selected from the group consisting of an EEPROM, a flash memory, and a logic circuit.

37. The implantable medical device of claim 33, wherein the first back-up memory also has stored therein at least one safe-mode parameter value.

38. The implantable medical device of claim 33, wherein the second back-up memory is a non-volatile, non-programmable memory.

39. The implantable medical device of claim 33, further comprising
   (d) a telemetry unit providing communication between the implantable medical device and an external programmer.

40. The implantable medical device of claim 33, further comprising:
   (d) means for restoring the main memory, upon a main memory failure, by copying the customized parameter value from the first back-up memory.

41. The implantable medical device of claim 33, further comprising:
   (d) means for restoring the main memory, upon a main memory failure, by copying the safe-mode parameter value from the second back-up memory.

42. A method of restoring treatment therapy from within an implantable medical device, comprising the steps of:
   (a) looking to a main memory for at least one parameter value;
   (b) if the main memory is corrupted, looking to a first back-up memory for a customized parameter value;
   (c) if the first back-up memory is not corrupted, reading the customized parameter value; and
   (d) if the first back-up memory is corrupted, reading a safe-mode parameter value from a second back-up memory.

43. The method of restoring treatment therapy of claim 42, further comprising the step of:
   (e) if the first back-up memory is not corrupted, copying the customized parameter value to the RAM.

44. The method of restoring treatment therapy of claim 42, further comprising the step of:
   (e) if the first back-up memory is corrupted, copying the safe-mode parameter value from the second back-up memory to the main memory.

45. The method of restoring treatment therapy of claim 42, further comprising the step of:
  (e) using an external programmer to update the customized parameter value via telemetry.

46. The method of restoring treatment therapy of claim 42, wherein the parameter value corresponds to a therapy parameter.

47. The method of restoring treatment therapy of claim 46, wherein the implantable medical device is an implantable pump and wherein the therapy parameter is selected from the group consisting of drug dosage amount, drug dosage rate, drug dosage timing, and drug dosage frequency.

48. The method of restoring treatment therapy of claim 42, wherein the parameter value corresponds to a trim parameter selected from the group consisting of bias current, reference voltage, and resistance.

49. A computer-readable medium having computer-executable instructions for performing the steps recited in claim 42.

* * * * *